United States Patent [19]

Callegaro et al.

[11] Patent Number: 5,646,129
[45] Date of Patent: Jul. 8, 1997

[54] METHOD OF USING LOW MOLECULAR WEIGHT HYALURONIC ACID FOR STIMULATING BONE FORMATION

[75] Inventors: Lanfranco Callegaro, Padova; Aurelio Romeo, Rome, both of Italy

[73] Assignee: Fidia S.p.A., Abano Terme, Italy

[21] Appl. No.: 318,804

[22] PCT Filed: Apr. 16, 1993

[86] PCT No.: PCT/EP93/00932

§ 371 Date: Jan. 17, 1995

§ 102(e) Date: Jan. 17, 1995

[87] PCT Pub. No.: WO93/20827

PCT Pub. Date: Oct. 28, 1993

[30] Foreign Application Priority Data

Apr. 17, 1992 [IT] Italy ................... PD92A0071

[51] Int. Cl.⁶ .................................... H61K 31/715
[52] U.S. Cl. .................................... 514/54; 514/62
[58] Field of Search .................... 536/18.7, 53, 55, 536/55.2, 55.1; 514/54, 62; 523/113, 114, 115

[56] References Cited

U.S. PATENT DOCUMENTS 5,079,236  1/1992  Drizen et al. ............... 514/54
5,137,875  8/1992  Tsunenaga et al. .......... 514/21

FOREIGN PATENT DOCUMENTS 2041539   11/1991  Canada .
0138572   4/1985   European Pat. Off. .
62-201825 9/1987   Japan .
2215209   9/1989   United Kingdom .
90/12603  11/1990  WIPO .

Primary Examiner—Gary L. Kunz
Assistant Examiner—Kathleen Kahler Fonda
Attorney, Agent, or Firm—Birch, Stewart, Kolasch & Birch, LLP

[57] ABSTRACT

The present invention is drawn to hyaluronic acid fractions having molecular weights in the range of from about 20,000 to about 60,000 daltons, wherein these hyaluronic acid fractions possess osteoinductive activity. The present invention further includes pharmaceutical compositions comprising such hyaluronic acid fractions to be used in the treatment of various types of bone disorders, as well as methods of treating such disorders using the pharmaceutical compositions.

3 Claims, 3 Drawing Sheets

METHOD OF USING LOW MOLECULAR WEIGHT HYALURONIC ACID FOR STIMULATING BONE FORMATION

This application is the U.S. national stage entry under 35 U.S.C. 371 of PCT/EP93/00932, filed on Apr. 16, 1993.

BACKGROUND OF THE INVENTION

1. Field of the Invention

The present invention relates to the use of various fractions of hyaluronic acid as osteoinductive agents, i.e., agents capable of stimulating the growth and differentiation of bone forming cells, and therefore the formation of new bone material itself. The type of activity refers to cells of mammalian origin.

2. Description of Related Art

An intricate network of macromolecules constituting the extracellular matrix, a substantial part of the tissue volume, largely fills the extracellular space. In many tissues, such as connective tissues, it is generally more abundant and completely surrounds the cells on all sides, thus determining the physical properties of the tissue. The extracellular matrix is of considerable importance in regulating many processes of tissue behavior. It has been demonstrated that changes in the state and composition oft he extracellular matrix profoundly influence biosynthetic processes and tissue development.

Glycosaminoglycans (GAGs) are the most plentiful non-fibrous, extracellular macromolecules, and are ubiquitous in all connective tissues. This group of high molecular weight anionic glycoconjugates is present in both the soft and mineralized connective tissues. They are substantially composed of large molecules called "non-collagenous proteins" (NCP) of the extracellular matrix, or "proteoglycans". The first of these terms distinguishes these molecules from the group of fibrous proteins such as collagen, elastin, fibronectin and laminin; the second indicates that they are usually found to be covalently bound to protein.

The biological properties of proteoglycans have been the object of intense research, mainly with regard to the soft tissues. The bone and cement, on the other hand, have been virtually ignored as far as their proteoglycan content is concerned. In fact, there is only one report in existence which describes the proteoglycans of the alveolar bone (R. J. Waddington et al., *Connective Tissue Res.*, 1988: 17, 171).

GAGs are long, unbranched polysaccharide chains composed of repetitive disaccharide units. The type of sugar residues, their bonds, and the number and position of the sulfate groups have led to the identification of four main groups of GAGs: 1) hyaluronic acid, 2) chondroitin solfate and dermatan sulfate, 3) heparan sulfate and heparin, and 4) keratan sulfate. It is important to note that GAGs (with the probable exception of hyaluronic acid) rarely exist in a free state within tissues. They are usually covalently bound to proteins.

With the exception of hyaluronic acid, GAGs contain sulfate groups, which together with carboxy groups, form a molecule with a highly negative charge under physiological conditions.

Hyaluronic acid (HA), also called hyaluronan or hyaluronate, contains up to several thousand sugar residues. It is a relatively simple molecule composed of regular sequences of non-sulfated disaccharide units.

HA is considered capable of facilitating cell migration during morphogenesis and tissue repair. It is found in varying quantities in all tissues and fluids in adult animals, and is particularly abundant in early embryos. Because of its simplicity, HA could represent the earliest evolutionary form of glycosaminoglycan. There is a correlation between HA production and mesenchymal cell movement on the one hand, and between HA distribution and cell differentiation on the other (B. Toole et al., *Proc. Nat. Acad. Sci., USA*, 1972: 69, 1384). The wound healing process possesses some aspects in common with early events which occur during the embryonic development of many organs, and HA plays an important role in both processes (B. P. Toole (1976) in S. H. Barondes, Ed., *Neuronal Recognition*, Plenum Press, New York, pp. 275–329); a correlation has been found between HA and cell adhesion, in terms of HA receptors (Goldstein et al., *Cell*, 1989: 56, 1063; I. Stamenkovic et al, *Cell*, 1989: 56, 1057).

Most of the characteristics of HA noted above for connective tissue can also be observed in bone. The probability that noncollagenous proteins influence local calcification mechanisms was assessed some time ago (H. Iwata et al., *Clin. Orthop., Rel. Res.* 1973: 90, 236; M. R. Urist, in Bourne, G. H. ed.: *The Biochemistry and physiology of Bone*, New York, Academic Press, 1976: 1–59). There are a number of interrelationships between HA and bone formation:

1. HA is a prominent component of the extracellular matrix during morphogenesis of bone (B. Toole et al., *Develop. Biol.*, 1971: 26, 28; H. Iwata et al., *Clin. Orthop., Rel. Res.*, 1973: 90, 236);

2. Considerable quantities of HA are present during the transition of mesenchymal cells to cartilage (O. Wiebkin et al., *FEBS Lett.*, 1973: 37, 42; C. H. Handley et al., *Biochem. Biophys. Acta*, 1976: 444, 69);

3. In terms of its correlation with wound healing processes and bony tissue development (B. P. Toole (1976) in S. H. Barondes, Ed., *Neuronal Recognition*, Plenum Press, New York, pp. 275–329), HA can be considered as a sort of "primer".

It has long been known that HA is useful in the treatment of periodontal diseases (*Minerva Stomatol.* 17: 140, 1968; *Riv. Ital., Stomatolog.* 20: 1540, 1965). There seems to be well-defined sequence of events in these cases:

—First, a HA-rich matrix is deposited in a space poorly furnished with cells;

—Secondly, cell migration is stimulated and the HA matrix is infiltrated by cells migrating from adjacent tissues; and —Lastly, the cells inside the extracellular matrix secrete hyaluronidase (which degrades the HA), sulfated glycosaminiglycans, and collagen, which replace part of the HA while the matrix becomes remodelled.

In each of the three developmental systems noted above, the HA matrix is first synthesized and then degraded. Consequently, it is probable that this transitory HA matrix, poor in cells, is needed before the complicated series of cell-mediated events which follows its destruction can proceed.

The presence of a certain number of sites binding HA onto the different types of cell surfaces has also been reported, such as in endothelial cells and fibroblasts (S. Eriksson et al., *Exp. Cell Res.* 1983: 144, 223; R. H. Raja et al., *J. Cell. Biol.;* 1985: 101, 426a; C. B. Underhill et al., *Cell Biol.* 1979: 82, 475). Thus, HA is able to interact specifically both with the cell surfaces and with the molecules of the extracellular matrices.

The chemical and physical-chemical characteristics involved in HA's osteoinductive activity have not yet been identified. It is known that the biological activity of hyaluronic acid can often be associated with definite fractions of different molecular weights and viscosity.

SUMMARY OF THE INVENTION

Therefore, an object of the present invention is to provide different fractions of hyaluronic acid extracted and purified from a source other than that of the cells on which it is to exert osteoinductive activity. Starting from the raw material, it is possible to obtain a substantially pure fraction of hyaluronic acid with a molecular weight in the range from about 20 to about 60 Kdaltons, a viscosity in the range from about 1.2 dl/g to about 2.8 dl/g, and a protein content of less than about 0.5% (weight/weight).

Another object of the present invention is to provide a pharmaceutical composition, comprising a hyaluronic acid fraction possessing osteoinductive activity, and a pharmaceutically acceptable carrier. Said pharmaceutical composition can be in the form of microspheres, membranes, films, non-woven tissues, tubes, nerve channels, sponges, a powder, or granules, and can contain from 0.1% to 99% by weight of said hyaluronic acid fraction, more preferably from 10% to 90% by weight of said hyaluronic acid fraction, and most preferably from 20% to 80% by weight of said hyaluronic acid fraction.

Further objects of the present invention include providing methods, useful in human and veterinary medicine, of maintaining bone function, of preventing the loss of bone function, of recovering bone function under traumatic conditions, of recovering bone function in acute or chronic pathological conditions, including acute pathological conditions in a late stage and chronic degenerative pathological conditions, and of treating pathological conditions caused by bone aging. These methods comprise administering to a human or animal in need thereof an effective amount of a pharmaceutical composition comprising a hyaluronic acid fraction possessing osteoinductive activity and a pharmaceutically acceptable carrier.

Said pharmaceutical composition can be administered by a route selected from the group consisting of parenteral administration, intradermal administration, local administration, and topical administration. Local administration can include intragingival application at the site of bone defects.

Further scope of the applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which.

DETAILED DESCRIPTION OF THE INVENTION

Figure 1:
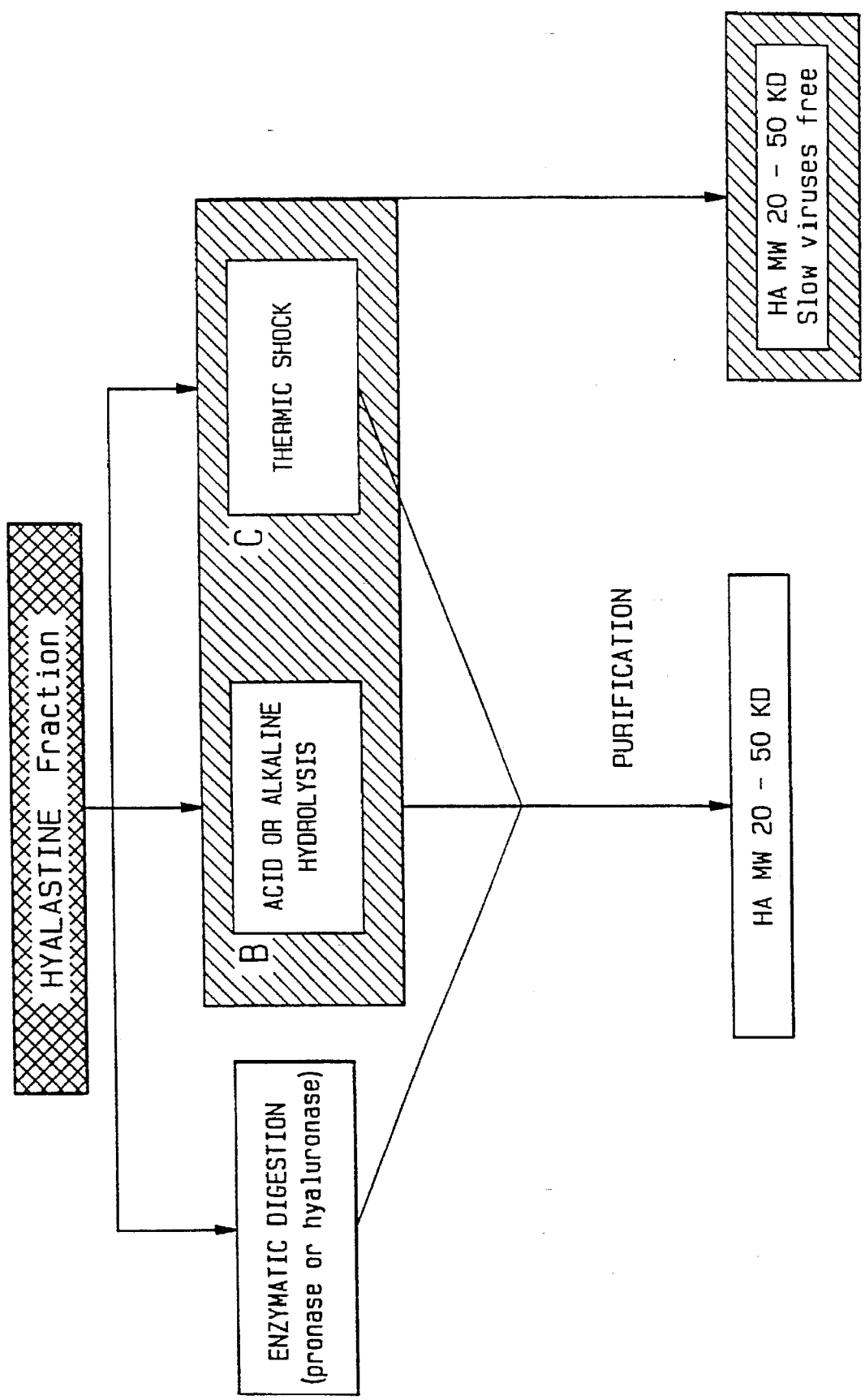
FIG. 1 shows various methods employed to produce the low molecular weight fractions of hyaluronic acid described herein.

The following detailed description is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited herein are incorporated by reference in their entirety.

MATERIALS AND METHODS

Preparation of Low Molecular Weight Hyaluronic Acid Fractions from Hyalastine

EXAMPLE 1

Method for obtaining a mixture of HYALASTINE and HYALECTIN fractions without inflammatory activity Hen crests, either fresh or frozen (3000 g), are minced in a meat mincer and then carefully homogenized in a mechanical homogenizer. The resulting paste is placed in an AISI 316 stainless steel container or in a glass container with 10 volumes of anhydrous acetone. The entire content is then agitated for 6 hours at a speed of 50 g/minute and left to separate for 12 hours, after which the acetone is syphoned off and discarded.

This extraction process is repeated until the discarded acetone has reached the correct humidity level (Karl-Fischer method).

The resulting substance is then centrifuged and vacuum dried at a suitable temperature for 5–8 hours. With this process, approximately 500–600 g of dry powder is obtained from the hen crests.

300 g of the dry powder is then submitted to an enzymatic digestion process with papain (0.2 g) through a buffered aqueous medium with a phosphate buffer in the presence of a suitable quantity of cysteine hydrochloride. This mixture is then agitated for 24 hours at 60 g/minute at a constant temperature of 60°–65° C. This whole mass is cooled to 25° C. adding 60 g of Celite (R) and the agitation is maintained for an additional hour.

The resulting mixture is filtered until a clear liquid is obtained. This clear liquid then undergoes molecular ultrafiltration by means of membranes with a molecular exclusion limit of 30,000 to retain on the membrane those molecules with a molecular weight of greater than 30,000. Five to six original volumes are ultrafiltered and, at the same time, distilled water is continually added to the product. The addition of distilled water is suspended and the product is ultrafiltered until it is reduced to one-third of its original volume.

The residue liquid is rendered 0.1M by adding sodium chloride and the temperature is brought to 50° C. 45 g of cetylpyridinium chloride is added while the product is being agitated at 60 g/minute. This mixture is agitated for 60 minutes, after which 50 g of Celite(R) is added. Under agitation the temperature of the product is reduced to 25° C. and the precipitate formed is collected by means of centrifugation. The precipitate thus obtained is suspended in a 0.01M solution of sodium chloride (5 liters) containing 0.05% cetylpyridinium chloride. It is agitated for a further 60 minutes at 50° C. The temperature is lowered to 25° C. and the precipitate centrifuged.

The washing process is then repeated three times and the precipitate finally gathered into containers holding 3 liters of a 0.05M solution of sodium chloride containing 0.05% of cetylpyridinium chloride. This is agitated at 60 g/minute for 60 minutes and maintained at a constant temperature of 25° C. for a period of 2 hours. The lipid supernatant is eliminated by means of centrifugation.

The procedure is thus repeated several times with a 0.1M sodium chloride solution containing 0.05% of cetylpyridinium chloride. The mixture is centrifuged and the supernatant discarded. The precipitate is dispersed in a 0.30M sodium chloride solution containing 0.05% of cetylpyridiniumchloride (3 l). The mixture is agitated and both the precipitate and the clear liquid are gathered. Extraction is repeated on the precipitate an additional 3 times, each time using 0.5 liters of the same aqueous solution.

Finally, the residue precipitate is eliminated and the clear liquids united in a single container. The temperature of the liquid is increased to 50° C. while agitating. The liquid is then brought to 0.23M with sodium chloride. 1 g of cetylpyridinium chloride is added and agitation maintained for 12 hours. The mixture is cooled to 25° C. then filtered, first through Celite(R) packs and then through a filter (1 μ).

The resultant mixture then undergoes a further molecular ultrafiltration through membranes with a molecular exclusion limit of 30,000, ultrafiltering 3 original volumes with the addition of a 0.33M sodium chloride solution. The addition of the sodium chloride solution is suspended and the volume of the liquid reduced to a quarter of its original volume.

The solution thus concentrated is precipitated under agitation (60 g/minute) at a temperature of 25° C. with three volumes of ethanol (95%). The precipitate is collected by centrifugation and the supernatant discarded. The precipitate is dissolved in 1 liter of 0.1M sodium chloride solution and the precipitation procedure is repeated with three volumes of 95% ethanol.

The precipitate is gathered and washed, first with 75% ethanol (three times), then with absolute ethanol (three times) and thirdly with absolute acetone (three times).

The product thus obtained (HYALASTINE+ HYALECTIN fraction) has an average molecular weight between 250,000 and 350,000.

The hyaluronic acid yield is equal to 0.6% of the original fresh tissue.

EXAMPLE 2

Method for obtaining the HYALASTINE fraction from the mixture obtained by the method described in Example 1

The mixture obtained by the method described in Example 1 is dissolved in pyrogen free distilled water in proportions of 10 mg of product in 1 ml of water. The solution thus obtained undergoes molecular ultrafiltration through membranes with a molecular exclusion limit of 200,000 with a concentration technique and without addition of water on the membrane. During the ultrafiltration process through membranes with an exclusion limit of 200,000, molecules with molecule weight greater than 200,000 will not pass, whereas smaller molecules will pass through the membrane along with the water; During the filtration process no water is added in the compartment above the membrane; therefore, the volume in this compartment will decrease, along with an increase in the concentration of molecules with M.W. over 200,000. It is then ultrafiltered until the volume on the membrane is reduced to 10% of the initial volume. Two volumes of pyrogen free bidistilled water are added and the solution is again ultrafiltered until the volume is reduced to one-third. The operation is repeated another two times.

The solution which passes through the membrane is brought to 1.0M with sodium chloride and then precipitated with four volumes of ethanol at 95%. The precipitate is washed three times with 75% ethanol and then vacuum dried.

The product thus obtained (HYALASTINE fraction) has an average molecular weight between 50,000 and 100,000.

The hyaluronic acid yield is equal to 0.4% of the original fresh tissue.

The low molecular weight hyaluronic acid fractions of the present invention were prepared from the hyalastine fraction as shown in FIG. 1.

Method for the cultivation of isolated mesenchymal cells

Swiss Webster mice at their 12th–13th day of pregnancy were anesthetized with 0.4 ml of sodium nembutal administered intraperitoneally. The fetuses were removed under sterile conditions. The epithelium was removed from the head, and the crown lifted to reveal the brain. Portions of the temporal, frontal, parietal and occipital mesenchyme were removed and immediately placed in BGJb medium. The tissue from each mouse was placed separately in a sterile Petri dish containing 12 ml of sterile Hank's balanced saline solution (HBSS) without calcium or magnesium, 10 mg of raw collagenase, and 50 μg of dextrose. The Petri dish was placed on a rotating platform and the tissue dissociated by crushing for 90 minutes at 37° C. The tissue thus dispersed was transferred to a sterile, conical 50 ml test tube for centrifugation. After centrifugation, the supernatant was removed and the resulting pellet was resuspended in BGJb medium enriched with 50 μg/ml gentamycin and 10% heat-inactivated fetal calf serum (checked for the absence of viruses). This procedure is repeated three times to ensure complete removal of collagenase. After the final resuspension, an aliquot is transferred to a hemocytometer for the determination of cell numbers. If the values obtained from the two chambers of the hemocytometer differ by more than the square root of the mean from the two chambers, the count is repeated. The cell suspension is then diluted or concentrated until a concentration of $4 \times 10^5$ cells/ml is obtained. Aliquots of 5 ml, each containing $2 \times 10^6$ cells, are placed in sterile, 60-mm Petri dishes and stored at 37° C., 100% humidity, in an atmosphere of 95% compressed air and 5% carbon dioxide. These cells develop into numerous bone colonies, as described by Marvaso and Bernard (J. S. Ko et al., Am. J. Anat. 1981: 161, 415).

Microscopy

The bone cultures are fixed in situ and subsequently removed intact from the Petri dishes with a rubber scoop, and gently packed by low-speed centrifugation. By sectioning the cell cultures thus treated, it is possible to see many areas of the culture, including their reciprocal relationships, and therefore to obtain an overall impression of the histological representation in each Petri dish. After fixing, all the tissue is dehydrated by passage through a series of alcohols, clarified with xylene, and embedded in paraffin. The area covered by each bone colony is measured by a digital analyzer connected to a phase contrast microscope (35×). Sections of 5–6 microns are taken from along the entire length of the material and mounted in a semiserial manner. Three consecutive sections of each row of 15 are stained in the same order with toluidine blue, H. and E, or neutral red, having been treated with Von Kossa reagents for the determination of bound calcium. All sections of a given tissue are examined, and the most representative microscopic fields are photographed.

The control skulls, the isolated mesenchymal cell pellets, and the cell culture material are collected and fixed as described above, with the difference that the cell cultures are not removed from the Petri dishes, but are fixed in situ. All the tissues are then post-fixed for one hour in 1% osmium tetroxide in 0.1M sodium cacodylate at pH 7.4, dehydrated in alcohol and propylene oxide or hydroxypropylmethacrylate and embedded in Epon 812. The blocks are cut with glass blades on a Porter-blum MT-1 ultramicrotome. For optical microscopy, semi-thin 1 micron sections of plastic material are stained with aqueous toluidine blue, while other thin sections are stained with uranyl acetate and lead citrate and used for all the ultrastructural analyses. Electron microscopy was performed with a Siemens 1A Elmskop at 80 KV. Within the cell cultures, only the clumps which represent cell aggregates of bone colony are examined. At least three clumps are chosen at random from each Petri dish, embedded at the set times.

EXAMPLE 3

Different quantities of Ha with different molecular weights were added to the cultured bone colonies, prepared as previously described.

The samples of HA, in powdered form, represented different molecular weight fractions of hyaluronic acid: $2 \times 10^4$; $4 \times 10^4$; $6 \times 10^4$; $16 \times 10^4$; $55 \times 10^4$; $88 \times 10^4$; and $13 \times 10^5$.

The characteristics of the HA samples, identified as A thru G, are shown in Table 1

TABLE 1

| Sample Code | Mean molecular weight (d × $10^{-3}$) | Intrinsic Viscosity dl/g | % albumin proteins |
|---|---|---|---|
| A | 20 | 1.20 | <0.5 |
| B | 40 | 1.3 | <0.5 |
| C | 60 | 2.8 | 0.3 |
| D | 160 | 4.8 | 0.4 |
| E | 550 | 12.1 | 0.2 |
| F | 800 | 10.0 | 0.2 |
| G | 1300 | 21.0 | 0.1 |

The various HA samples were used to treat mesenchymal cells at three different concentrations: 0.5, 1.0 and 2.0 mg/ml. All samples were administered to a total of 8 Petri dishes per test to yield statistically significant data. The culture medium (BGJb) containing HA was first replaced with HA-free medium after 48 hours, and then every 24 hours thereafter until day 10, when the resulting tissues were fixed.

The photomicroscopic results showed the greatest osteoinductive activities in samples A, B and C.

Figure 2:
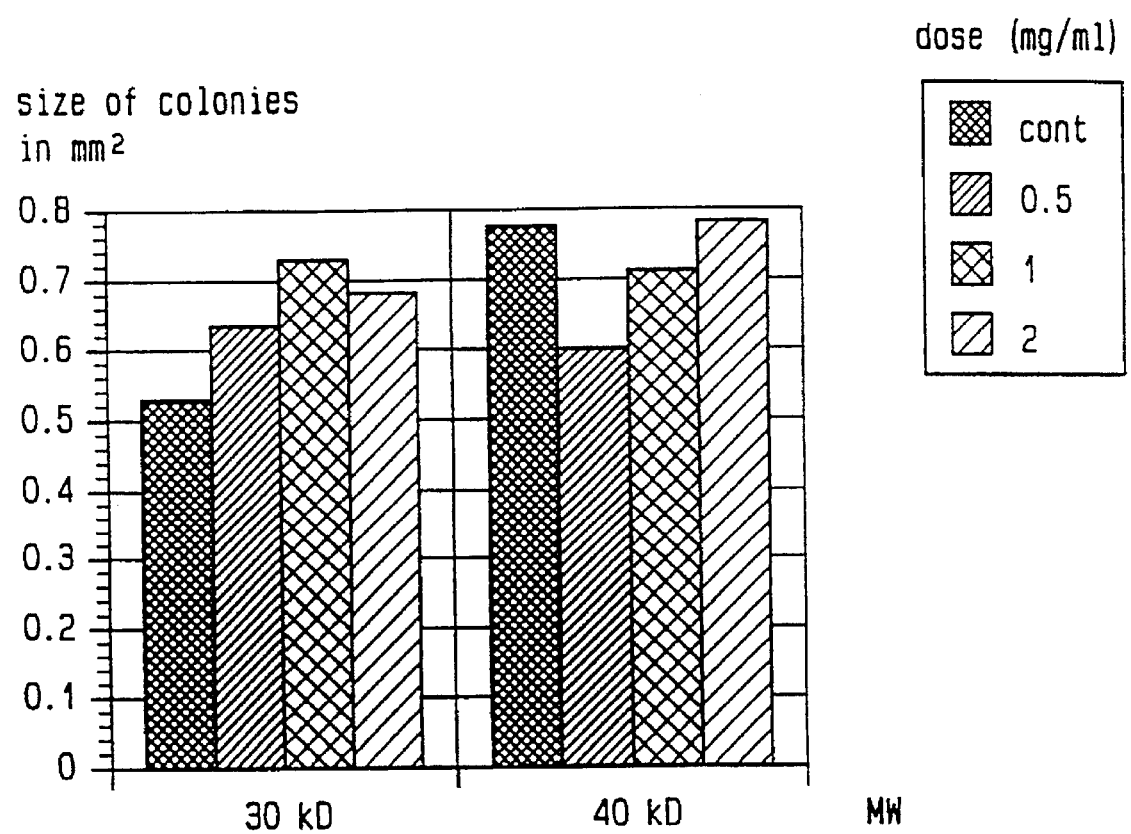
FIG. 2 shows the osteoinductive activity in vitro, as measured in terms of bone colony area, of hyaluronic acid fractions having molecular weights of 30 and 40 Kdaltons at concentrations of 0.5, 1.0, and 2.0 mg/ml.
Figure 3:
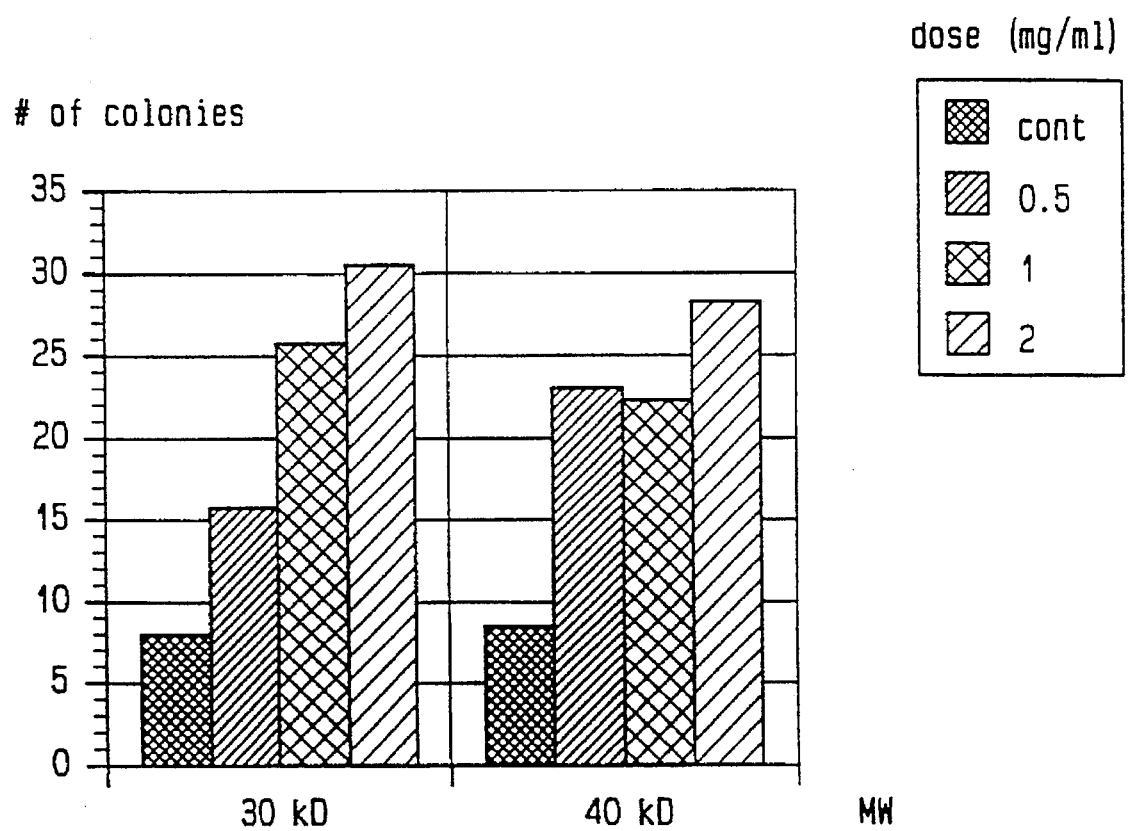
FIG. 3 shows the osteoinductive activity in vitro, as measured in terms of bone colony number, of hyaluronic acid fractions having molecular weights of 30 and 40 Kdaltons at concentrations of 0.5, 1.0, and 2.0 mg/ml.

FIGS. 2 and 3 show the effects of HA fractions having molecular weights of 30 and 40 Kdaltons on colony area and colony number, respectively, in cultured bone colonies.

As shown in FIG. 2, the HA fraction with a molecular weight of 30 Kdaltons (left panel) was most effective in stimulating bone colony area development at a concentration of 1 mg/ml. The HA fraction with a molecular weight of 40 Kdaltons was most effective at a concentration of 2 mg/ml (right panel). In both cases, the relationship between colony size and HA dose was roughly linear.

As shown in FIG. 3, both the 30 and 40 Kdalton HA fractions were most effective in stimulating colony formation at 2 mg/ml. Treatment with both HA fractions induced a marked increase in the number of bone colonies in culture as compared to non-treated controls. This increase was roughly linear with increasing dose, and was more evident with the 30 Kdalton HA fraction.

The invention being thus described, it is obvious that the same can be modified in various ways. Such modifications are not to be considered divergences from the spirit and scope of the present invention, and any modification that would be apparent to one skilled in the art is to be considered as coming within the scope of the following claims.

We claim:

1. A method of stimulating growth of bone forming cells comprising exposing mesenchymal cells to hyaluronic acid having a molecular weight of 20–60 kD.

2. The method of claim 1, wherein said hyaluronic acid has a viscosity in the range of from 1.2 dl/g to 2.8 dl/g.

3. The method of claim 1, wherein said hyaluronic acid has a protein content of less than 0.5%.

* * * * *